US012123930B2

(12) United States Patent
Fenchel et al.

(10) Patent No.: US 12,123,930 B2
(45) Date of Patent: Oct. 22, 2024

(54) RF COIL DEVICE FOR AN MR-PET IMAGING MODALITY AND METHOD TO DETERMINE THE POSITION AND/OR ORIENTATION AND/OR SHAPE OF AN RF COIL DEVICE

(71) Applicant: Siemens Healthcare GmbH, Erlangen (DE)

(72) Inventors: Matthias Fenchel, Erlangen (DE); Ralf Ladebeck, Erlangen (DE); Johann Sukkau, Herzogenaurach (DE)

(73) Assignee: Siemens Healthineers AG, Erlangen (DE)

( * ) Notice: Subject to any disclaimer, the term of this patent is extended or adjusted under 35 U.S.C. 154(b) by 49 days.

(21) Appl. No.: 17/204,351

(22) Filed: Mar. 17, 2021

(65) Prior Publication Data
US 2021/0293915 A1    Sep. 23, 2021

(30) Foreign Application Priority Data
Mar. 18, 2020 (EP) .................................... 20163901

(51) Int. Cl.
*A61B 5/00* (2006.01)
*A61B 5/055* (2006.01)
(Continued)

(52) U.S. Cl.
CPC .......... *G01R 33/481* (2013.01); *A61B 5/0035* (2013.01); *A61B 5/055* (2013.01);
(Continued)

(58) Field of Classification Search
CPC ............ G01R 33/481; G01R 33/34092; G01R 33/5608; G01R 33/34; G01R 33/58;
(Continued)

(56) References Cited

U.S. PATENT DOCUMENTS 6,317,619 B1 * 11/2001 Boernert .............. G01R 33/341
600/410
9,547,055 B2    1/2017 Biber et al.
(Continued)

FOREIGN PATENT DOCUMENTS

EP          3335664 A1 *  6/2018  ............. G01C 11/00
KR      20120069459 A     6/2012
WO         0109633 A2     2/2001

OTHER PUBLICATIONS

Fenchel, M. Dr., "Quality Guard for Hardward Attenuation Correction in MR-PET," Siemens AG, file: 2019E11206DE.doc, pp. 1-2 (2019).
(Continued)

*Primary Examiner* — Joel Lamprecht
*Assistant Examiner* — Gabriel Victor Popescu
(74) *Attorney, Agent, or Firm* — Banner & Witcoff Ltd.

(57) ABSTRACT

The disclosure relates to an RF coil device for an MR or hybrid MR-PET imaging modality, the RF coil device having a marker arrangement comprising a plurality of electromagnetic radiation markers disposed at the outer surface of its housing, wherein the electromagnetic radiation markers are adapted to reflect or emit electromagnetic radiation within the ultraviolet, visible, infrared (IR) and/or Terahertz spectrum. The disclosure also relates to detecting the position and/or orientation and/or shape of the RF coil device using electromagnetic radiation emitted from the electromagnetic radiation markers, and determining an attenuation map for the RF coil device by transforming a predefined attenuation map using the determined position and/or orientation and/or shape of the RF coil device.

17 Claims, 8 Drawing Sheets

(51) Int. Cl.
  *A61B 6/00* (2006.01)
  *A61B 6/03* (2006.01)
  *G01R 33/34* (2006.01)
  *G01R 33/48* (2006.01)
  *G01R 33/56* (2006.01)

(52) U.S. Cl.
  CPC ............ *A61B 6/037* (2013.01); *A61B 6/4417* (2013.01); *G01R 33/34092* (2013.01); *G01R 33/5608* (2013.01)

(58) Field of Classification Search
  CPC . G01R 33/34084; A61B 5/0035; A61B 5/055; A61B 6/037; A61B 6/4417
  See application file for complete search history.

(56) References Cited

U.S. PATENT DOCUMENTS

| | | | |
|---|---|---|---|
| 9,658,299 B2 | 5/2017 | Paul | |
| 9,726,470 B2 | 8/2017 | Biber et al. | |
| 10,908,238 B2* | 2/2021 | Gross | A61B 5/055 |
| 2005/0154283 A1* | 7/2005 | Wright | A61B 5/06 |
| | | | 600/407 |
| 2009/0005677 A1* | 1/2009 | Weber | A61B 6/04 |
| | | | 600/426 |
| 2009/0105583 A1 | 4/2009 | Martin et al. | |
| 2009/0195249 A1* | 8/2009 | DeMeester | G01R 33/421 |
| | | | 324/318 |
| 2009/0278049 A1 | 11/2009 | Ladebeck | |
| 2010/0156421 A1* | 6/2010 | Sukkau | G01R 33/3415 |
| | | | 324/318 |
| 2010/0182005 A1 | 7/2010 | Biber | |
| 2013/0267830 A1 | 10/2013 | Ojha et al. | |
| 2014/0159728 A1* | 6/2014 | Wirtz | G01R 33/28 |
| | | | 324/322 |
| 2015/0031981 A1 | 1/2015 | Candidus et al. | |
| 2015/0045655 A1* | 2/2015 | Biber | G01R 33/58 |
| | | | 600/414 |
| 2015/0087958 A1 | 3/2015 | Kartmann et al. | |
| 2015/0190107 A1 | 7/2015 | Kim et al. | |
| 2015/0219737 A1 | 8/2015 | Fenchel et al. | |
| 2016/0073962 A1 | 3/2016 | Yu et al. | |
| 2016/0135711 A1 | 5/2016 | Dohata et al. | |
| 2016/0216345 A1 | 7/2016 | Greim | |
| 2016/0259019 A1 | 9/2016 | Gross et al. | |
| 2017/0103287 A1 | 4/2017 | Han | |
| 2017/0248665 A1 | 8/2017 | Ludwig et al. | |
| 2017/0311841 A1 | 11/2017 | Rothgang | |
| 2018/0074144 A1* | 3/2018 | Dezorayev | G01R 33/34046 |
| 2019/0029559 A1 | 1/2019 | Nufer et al. | |
| 2019/0374105 A1 | 12/2019 | Raylman et al. | |
| 2019/0377040 A1* | 12/2019 | Stack | G01R 33/34053 |
| 2020/0107725 A1* | 4/2020 | Tyler | A61B 5/0035 |

OTHER PUBLICATIONS

Kartmann et al., "Integrated PET/MR imaging: Automatic attenuation correction of flexible RF coils," Medical Physics, vol. 40, No. 8, pp. 082301-1-082301-14 (2013).

Fenchel et al., "Plug-and-Play Hardware Attenuation Correction in MR-PET," Siemens AG, file: 2019E16535DE.doc, pp. 1-2 (2020).

European Search Report for German Application No. 20163901.0, dated Sep. 9, 2020.

Anonymous: "Liquid-crystal display", Wikipedia, Mar. 8, 2020 (Mar. 8, 2020), XP093073242.

* cited by examiner

RF COIL DEVICE FOR AN MR-PET IMAGING MODALITY AND METHOD TO DETERMINE THE POSITION AND/OR ORIENTATION AND/OR SHAPE OF AN RF COIL DEVICE

CROSS-REFERENCE TO RELATED APPLICATIONS

The present application claims the benefit of the filing date of European patent application no. EP 20163901.0, filed on Mar. 18, 2020, the contents of which are incorporated herein by reference in their entirety.

TECHNICAL FIELD

The disclosure relates to an RF coil device for a magnetic resonance (MR) or MR-PET (positron emissions tomography) imaging modality, a method to determine the position and/or orientation and/or shape of an RF coil device, a storage medium, and a hybrid MR-PET imaging modality.

BACKGROUND

Positron emission tomography (PET) is an imaging method to visualize metabolic processes. Thereby, positron emitting radionuclides bound to biologically-active molecules are brought into a patient. These molecules transport the radionuclides to the desired position in the body of the patient and allow the radionuclide to become part of the metabolism.

One exemplary molecule is fluorodeoxyglucose (18F) (FDG). Its enrichment marks places in the body where an increased glucose uptake takes place. Cancer metastases generally have an increased glucose uptake (Warburg effect), and this enrichment can be shown on PET images.

Positron emitting radionuclides emit positrons, which however are not detected directly but via annihilation events: after emission, the positrons travel through the body for about 1 mm until they interact with an electron. The annihilation of proton and electron causes a pair of photons having the characteristic energy of 511 keV to be emitted at 180° to each other. These photons have to be detected coincidently to be counted as an annihilation event. Therefore, a ring of PET detector elements is positioned around the patient.

To enhance the value of the PET images, they are often combined with a further imaging modality. PET-CT (computed tomography) and PET-MR (magnetic resonance) are well known examples of hybrid imaging modalities. PET-MR is promising because MR can display soft tissue. In a PET-MR hybrid imaging modalities, PET and MR images can be taken simultaneously or consecutively, but without changing the patient's position on the patient table, e.g. by moving the patient table translationally from a PET Field-of-View (FoV) to an MR Field-of-View (FoV), which are both situated inside the bore of the main MR magnet and either overlap each other or are shifted from one another along a direction of translation of the patient table, usually the z-direction.

In either case, the RF coil devices used for MR imaging, i.e. the radio frequency (RF) coils used for detecting the MR signal need to be placed close to the patient's body before the patient table is transferred into the magnet bore, and will thus be situated between the patient and the PET detector elements. This may cause problems because the RF coils will attenuate the PET signal. In the reconstruction of the PET images, the expected attenuation of the photons may be taken into account. Otherwise, positions suffering from PET signal attenuation, e.g. areas deeper in the body or areas screened by the RF coils, seem to take up lower concentrations of the radionuclide. Therefore, an attenuation map is needed for compensation and correction for the loss of photon counts.

If the density of an RF coil device and in particular of its coils at the PET energy of 511 keV and its position are known, the RF coil device can be included in the attenuation map. However, this requires knowledge of the exact position of the RF coil device during the particular measurement, and it is difficult to determine the position of the RF coil device in a hybrid MR-PET imaging modality, since it cannot be captured on either MR or PET images.

In hybrid CT-PET imaging modalities, an attenuation map of the equipment within the Field-of-View (FoV) like a patient table, cushions, etc., can be indirectly measured by converting the acquired CT image to the density at the energy of the PET photons at 511 keV. However, in MR-PET, the transmission can neither be measured directly nor indirectly. The approach for MR-PET so far was therefore to measure the attenuation of stationary fixed equipment a priory by a CT scan, and to apply this attenuation map at its known position to any PET scan. Regarding the non-stationary equipment, i.e. equipment which is sometimes but not always present within the FoV such as local RF coils used for MR imaging, the approach was to reduce the attenuation and density to an extent that its impact can be safely ignored. While this approach is viable for older generation coils like the TIM® 6 channel body matrix coil, RF coils with higher channel densities and more massive housings, like the TIM®4G coils, cannot be easily redesigned towards lower PET attenuation without impacting their performance. Here, it would be desirable to include their attenuation into the attenuation map used for correction of PET images.

SUMMARY

The object of the disclosure is therefore to provide an RF coil device and a method for determining an attenuation map of MR equipment, in particular of an RF coil device, which can be carried out quickly while or before performing a patient examination using an MR imaging modality or a hybrid MR-PET imaging modality. It is another object of the disclosure to provide a method of detecting the exact position, orientation, and shape of an RF coil device or other equipment within the FoV of an MR or MR-PET imaging modality.

These and further objects are met by the RF coil device according to the embodiments of the present disclosure and as described in the claims, which include as examples a method to determine the position, orientation, and/or shape of a coil, a computer-readable data storage medium, and a MR or a hybrid MR-PET imaging modality. Any features or embodiments described with regard to one category are also applicable to the other categories, e.g. any features described with regard to the RF coil device are also applicable to the described method and MR-PET imaging modality, and vice versa.

The RF coil device of the disclosure includes a marker arrangement comprising a plurality of electromagnetic radiation markers at the outer surface of the coil housing, which are adapted to reflect or emit electromagnetic (EM) radiation within the ultraviolet, visible, infrared (IR), and/or Terahertz spectrum, e.g. at a wavelength in any suitable range such as for instance between 10 nm and 3 mm or between 300 nm or 400 nm and 1 mm, i.e. within the visible or infrared (IR) spectrum. One or several EM radiation detectors or cameras sensitive to this particular EM radiation, in the case of IR light for example high-resolution CMOS cameras (3D or also 2D), may detect this light as a 3D mesh or grid of surface points. The position, orientation, and shape of the RF coil device and/or of the RF coils contained therein can then be detected by solving the 3D correspondence problem of these points with a known reference model of the RF coil device by methods known in computer vision. A predefined attenuation map of that RF coil device, which may have been obtained previously, e.g. by taking a CT image of the RF coil device, can be transformed (e.g. "warped") accordingly and copied to this position in the final attenuation map and hence correct the loss in counts during the PET reconstruction. Embodiments also include the marker arrangement comprising several electromagnetic radiation markers, e.g. LEDs, which can be controlled independently to switch individual surface points on and off in order to simplify the correspondence problem.

The RF coil device may comprise one or several coils. In a first embodiment, the RF coil device has one coil. In an alternative embodiment, the RF coil has at least two coils, for example an array of several coils. The coils are RF coils configured to receive and, in some embodiments, transmit MR signals. Thus, the resonant frequency of the coils may be within the shortwave radio portion of the electromagnetic spectrum, e.g. between about 10 MHz and 300 MHz, corresponding to main magnetic fields between about 0.25 T and 7 T, typically between about 42 MHz and 127 MHz (main magnetic field 1 T to 3 T). The RF coil device may be implemented as a local coil, i.e. one that is placed close to the patient to be examined before each examination, and not the body coil, which is fixedly integrated into an MR scanner. The RF coil device embodiments as described in the disclosure may be implemented both in a magnetic resonance apparatus and in a hybrid PET-MR imaging modality.

The housing of the RF coil device may be either flexible or inflexible, and may be made of plastic or rubber. The RF coil devices used in MR have at least one conductor. A variety of coil types are known, e.g. birdcage resonators, Helmholtz coils or surface coils, wherein surface coils often comprise an array of individual coils. While birdcage resonators and Helmholtz coils usually are combined with rigid housings, surface coils may be used with either flexible or inflexible housings. Many surface coils have flexible housings which can be bent, for example multi-channel coils such as the TIM®4G coils, which currently may have up to 204 coil elements within one RF coil device. Such flexible RF coil devices may for example have a housing of a flexible plastic or rubber, so that the RF coil device may be fitted around the body part to be imaged like a blanket.

In one embodiment, the RF coil device has an inflexible housing. In this case, a small number of e.g. 2-6 (e.g. three) electromagnetic radiation markers is sufficient to determine the position and orientation of the RF coil device by an electromagnetic radiation detector positioned e.g. above the RF coil device.

In another embodiment, the RF coil device has a flexible housing. If the housing is flexible there may be more than three electromagnetic radiation markers, for example dependent of the number of coils included in the RF coil device. For example, if the RF coil device comprises a number of N individual coils, which are arranged next to one another in a flexible, blanket-type housing, there may be between N and N+3 markers.

An electromagnetic radiation marker is an area where electromagnetic radiation is emitted or reflected. The frequency or frequency range of the electromagnetic radiation marker may be between any suitable frequency range such as, for instance, between 300 GHz and $3 \times 10^{16}$ Hz, between about 10 THz and 1000 THz (THz=TeraHertz, $10^{12}$ Hz), corresponding to a wavelength of about 10 nm to 3 mm, 300 nm to 1 mm, etc. Thus, the frequency of the marker differs from the resonant frequency or frequencies of the RF coil device and therefore does not affect the MR measurements. The frequency of the electromagnetic radiation marker may be a single frequency or a frequency distribution having a frequency range.

The electromagnetic radiation marker(s) are located at the outer surface of the housing the RF coil device. Then, the emitted electromagnetic radiation can be detected by an EM radiation detector outside the RF coil device. In an embodiment, the electromagnetic radiation markers are positioned at the upper side of the RF coil device, and the EM radiation detector is placed somewhere above the patient table. The electromagnetic radiation markers may form a characteristic pattern, e.g. a grid of points, which may be specific for each RF coil device.

In an embodiment, the marker arrangement has at least one electromagnetic radiation source, in which case the electromagnetic radiation marker is adapted to emit electromagnetic radiation. An electromagnetic radiation source may be designed as LED (light emitting diode), e.g. as infrared LED. As an example, commercially available infrared LEDs typically emit light having wavelengths such as 840 nm, 850 nm, 875 nm, 880 nm, 885 nm, 890 nm, 940 nm, 950 nm, etc. In an embodiment, the infrared LED may emit electromagnetic radiation of a wavelength of about 940 nm.

To realize several electromagnetic radiation markers, several electromagnetic radiation sources may be positioned at the surface of the RF coil device. Every electromagnetic radiation source is then an electromagnetic radiation marker.

The radiation sources may be implemented as light emitting diodes (LEDs) emitting optical or infrared radiation (light), for instance. Such LEDs may be distributed over the surface of the RF coil device to produce a characteristic three-dimensional pattern, which may be detected by the electromagnetic radiation detector, which is preferably an optical or infrared camera (depending on the type of radiation emitted). If the coils and other conductors and electronic components, which form part of the RF coil device are covered by a coil housing, the electromagnetic radiation sources may be placed within recesses in the housing so that can radiate light outward without obstruction. The LEDs may project slightly or not above the outer surface of the coil housing. In other embodiments, the radiation sources may be covered by a protective layer, which is permeable to the type of electromagnetic radiation emitted. The LEDs are connected to an electrical power supply of the RF coil device inside the coil housing. The advantage of having several electromagnetic radiation sources is that they may be controlled independently so as to be able to switch individual markers on and off. By detecting the respective markers one after the other in a defined order, the mathematical problem of identifying the position of each marker in three-dimensional (3D) space is simplified, since the markers cannot be confused with one another. However, the requirement to connect each radiation source individually to electrical current adds to the complexity of the coil.

Alternatively, the marker arrangement may comprise at least one electromagnetic radiation guide to distribute the electromagnetic radiation from the at least one electromagnetic radiation source to several electromagnetic radiation markers, wherein the radiation source may be positioned at the center of a coil, and the EM radiation guides may run from there towards the periphery of the RF coil arrangement, e.g. like a spider web below the surface. The radiation source may be positioned at any convenient location within the RF coil device, which may be embedded in and/or completely covered by the housing so that it cannot be seen directly from the outside. The radiation source may also be positioned close to the surface of the RF coil device, for example within a recess in the housing open towards the outside. By using EM radiation guides, several EM radiation markers may be realized with only one radiation source, thereby simplifying the need for electricity supply to the radiation markers or LEDs. An RF coil device may comprise only one or e.g. 1-20 radiation sources, which supply a larger number (e.g. 10 to 100) EM radiation markers. The EM radiation guides may be integrated into the housing just below the surface, e.g. open towards the outside, or covered by a permeable protective cover. In one embodiment, the electromagnetic radiation guides emit radiation at their respective ends. In another embodiment, the electromagnetic radiation guides emit radiation at several locations along their length, for example every 2-10 cm.

The marker arrangement may comprise at least one LED as electromagnetic radiation source and at least one optical fiber which distributes the electromagnetic radiation from the LED over the outer surface of the housing. In this embodiment, the electromagnetic radiation may be visible or infrared light, so that the electromagnetic radiation guides may be referred to as optical fibers or light guides. The optical fibers may run over the surface or the RF coil device in a characteristic pattern, wherein they may cross one another. For example, a number of optical fibers may run radially, thereby forming a cross or star having one or possibly several LED(s) in the center. Such radial light guides may be crossed by other light guides running circumferentially around the center of the star, thereby forming a spider-web, e.g. as seen from above. In other embodiments, several light guides may run in parallel, possibly crossed at approximately right angles by other light guides. In an embodiment, each optical fiber is guiding light from one LED. In other embodiments, one LED may supply several optical fibers. As an example, the optical fibers may emit (visible or IR) light towards the outside of the RF coil device at pre-defined distances along their length, or at pre-defined positions distributed over the outer surface of the coil housing. For example, there may be one electromagnetic radiation marker for approximately each 20-200 cm2 of coil surface.

To realize the individual electromagnetic radiation markers, the radiation may be emitted from openings in a coating of the optical fiber, wherein each opening corresponds to an electromagnetic radiation marker. For example, the openings may be at distances of 1-10 cm along the length of the optical fiber, and optionally at the end of the fiber (the end of an optical fiber usually also comprises an opening in the coating of the fiber). In this embodiment, each radiation marker cannot be switched on and off individually. However, if several LEDs are present, each feeding one or several optical fibers, it may still be possible to control parts of the marker arrangement individually so as to simplify the mathematical problem of finding the 3D position of each marker in space.

Of course, both embodiments can be combined. For example, a portion of the electromagnetic radiation markers may be realized by electromagnetic radiation sources and another portion of the electromagnetic radiation markers may be realized by the endings and/or holes in the coating of the electromagnetic radiation guides.

An alternative embodiment is the usage of at least one reflector as EM radiation marker. The reflectors may reflect electromagnetic radiation from one or several external electromagnetic radiation sources such as an optical or IR lamp. The lamp(s) may be placed next to the camera used for detecting the EM radiation from the marks. The reflectors may be small mirrors placed at the outer surface of the RF coil housing, or alternatively the housing may be coated with a shiny metal at pre-defined positions, wherein the shiny metal surfaces may form a distinctive pattern of EM radiation markers on the outer surface of the housing, such pattern comprising spots, dotted or dashed lines and possibly uninterrupted lines. The shiny metal surfaces act as reflectors. In this embodiment, there is no need for an additional electrical current connection within the RF coil device and additionally no electromagnetic radiation guides are necessary.

In some embodiments, the electromagnetic radiation is emitted or reflected by the electromagnetic radiation markers in a directional way. Neither the electromagnetic radiation emitted by the coil itself in the MR experiment, nor light scattered from the surface of the RF coil device are used in the described disclosure.

In an embodiment, the radiation emitted or reflected by the electromagnetic radiation marker is light, wherein light is defined to include infrared radiation (IR), visible light, and ultraviolet (UV) radiation. Infrared radiation has wavelengths from about 700 nm to 1 mm, visible light has wavelengths from 400 nm to 700 nm, and ultraviolet radiation has wavelengths from 10 nm to 400 nm.

In an embodiment, the electromagnetic radiation markers are designed to emit or reflect infrared radiation. Then, the electromagnetic radiation is not visible to the patient. Therefore, the electromagnetic radiation sources may emit the radiation intermittently to create a specialized radiation sequence without causing possible negative reactions to "flickering light" for the patient. Furthermore, if a wavelength is used which is not otherwise emitted from the RF coil device, the patterns of markers may be easily detected by the one or several cameras or video cameras, i.e. a grid of visible points is acquired which corresponds to the grid of electromagnetic radiation markers. In this embodiment, infrared LEDs and one or several low-cost 2D or 3D cameras may be used to detect the RF coil position based on the infrared emission signal, e.g. IR sensitive high-resolution CMOS cameras. These are standard, low-cost components, which are MR compatible. In addition, the infrared detection method is not prone to failure scenarios like occlusions by blankets. Furthermore, it does not suffer from the drawbacks of other methods in that it does not have a negative impact on either modality (e.g. MR visibility and potential fold-in artifacts of conventional markers, etc.).

In an embodiment of the disclosure, the cameras/video cameras/detectors used to detect the EM radiation emanating from the markers are infrared detectors, which may be sensitive to wavelengths from about 0.7 µm to about 14 µm. As an example, the detectors may at least partially detect wavelengths of the near-infrared spectrum (0.7 µm to 1.4 µm), short-wavelength infrared spectrum (1.4 µm to 3 µm), mid-wavelength infrared spectrum (3-8 µm), or the long-wavelength infrared spectrum (8-15 µm).

In another embodiment, the electromagnetic radiation markers are designed to emit so called Terahertz radiation, i.e. radiation having wavelengths in a range of about 30 µm to 3 mm, and may range up to 1 mm, which partially overlaps the range of far infrared radiation. Infrared detectors and Terahertz detectors both work within the range of infrared radiation but use different wavelengths. In this embodiment, the EM radiation source may be a THz laser, and the radiation guides may be hollow conductors, e.g. silver-coated. The cameras used to detect the THz radiation may be infrared cameras sensitive to thermal radiation. The advantage of this embodiment is that THz radiation can penetrate textiles and clothing, and thus a blanket placed over the patient for warmth is not an obstacle to the EM radiation.

In an embodiment, the RF coil device has several coils, and each coil has at least one electromagnetic radiation marker of its own. As an example, the marker may be placed at the outer surface of the housing in the center of the corresponding coil beneath it. That means that the position and orientation of each coil can be determined separately.

In accordance with another embodiment of the disclosure, a method to determine the position and/or orientation and/or shape of at least one coil of an RF coil device is provided. The RF coil device has electromagnetic radiation markers as described herein. The method comprises the steps:

positioning the RF coil device on a patient table of an MR imaging modality or a MR hybrid MR-PET imaging modality;

detecting the electromagnetic radiation emitted or reflected from a plurality of electromagnetic radiation markers on the surface of the RF coil device by means of an electromagnetic radiation detector;

determining the position and/or orientation and/or shape of the at least one coil of the RF coil device using the detected electromagnetic radiation.

In an embodiment, the method is carried out while the RF coil device is positioned on a patient lying on the patient table, e.g. before or while the MR or MR-PET examination is carried out. It is advantageous to be able to determine the exact position, orientation, and shape of an RF coil device, or at least one coil thereof, in a particular patient examination, because it allows e.g. to select an individual coil within the RF coil device, which is to be used in this examination. Further, the position/shape information may be used for quality control, e.g. to find out whether the body part to be examined is adequately covered by the coil. In an embodiment, the method steps are carried out repeatedly, and even continuously, before or during an MR or MR-PET examination. Thereby, the successive positions and/or orientations and/or shapes of the at least one coil of the RF coil device can be compared with each other, thereby allowing to detect a movement of the RF coil device. Such movement may be caused by patient movement, and may be used for correction of the MR or PET image acquisition.

The electromagnetic radiation detector may be adapted to detect the positions of the EM radiation markers in space, for example as a 3D mesh or grid of points (each point corresponding to a marker). This 3D mesh may then be compared with the known position of the markers on the RF coil device, and thereby the position, orientation, and shape of the RF coil device and/or of the RF coils contained therein can be determined. Methods for solving the 3D correspondence problem of the detected marker points with a known reference model of the RF coil device are known from computer vision.

In an embodiment, the method also comprises steps to determine an attenuation map for the RF coil device, e.g. the attenuation map is to be used in correcting a PET image acquired from a patient in a hybrid PET-MR imaging modality. The method comprises the further steps:

providing a predefined attenuation map of the RF coil device, determining the attenuation map for the RF coil device by transforming the predefined attenuation map using the determined position and/or orientation and/or shape of the at least one coil.

The idea of the described method is to transform or warp a known attenuation map for an RF coil device acquired in a known first position and/or orientation and/or shape of the RF coil device to match a second position and/or orientation and/or shape of said RF coil device, wherein the second position and/or orientation and/or shape is the one which the RF coil device will actually have during the patient examination by PET and MR in the MR-PET imaging modality while it is placed on the patient, and which is determined using the EM radiation markers.

From the new position, orientation, and/or shape of the RF coil device, a pre-defined attenuation map, which may include a map of the density of the RF coil device at the PET-energy of 511 keV, can be "warped" or transformed into the actual attenuation map. The predefined attenuation map may be obtained as described above using CT, or may be calculated from the known contents of the RF coil device, and may be stored on the MR-PET imaging modality for all available RF coil devices. In an embodiment, the predefined attenuation map not only comprises data on the attenuation of the RF coil device, but also includes the positions of the electromagnetic radiation markers. Thus, one has to solve the mathematical problem of finding a suitable transformation, which in the case of flexible RF coil devices needs to be a non-rigid transformation between the EM radiation markers in the predefined attenuation map, and the positions of the markers as determined by the camera(s). From the change in position of the plurality of markers, the change in orientation and/or shape follows.

Using the position information of the electromagnetic radiation markers and therefore of the RF coil device, the predefined attenuation map can be transformed to an updated, current attenuation map. The more precise the current position of the RF coil device is known, the better the attenuation map can be determined and the more precise the PET image can be reconstructed.

The position and/or orientation and/or shape of the RF coil device may be determined while the patient is lying on the patient table with the RF coil device in the correct position with respect to the patient's body, but while the patient table is (still) outside the hybrid PET-MR imaging modality. Thereby, the camera(s) need not be inside the magnet bore, but can be placed above the patient table (e.g. attached to the ceiling) and used to detect the EM radiation markers before the patient table is transferred into the FoV inside the magnet bore. Since usually this transfer is a simple translational movement, the detected position, shape and/or orientation of the RF coil device can easily be transformed to the new position inside the FoV.

Alternatively, the patient and the RF coil device are positioned inside the MR or hybrid PET-MR imaging modality prior to the determination of the position and/or orientation and/or shape of the RF coil device.

The RF coil device used in the detection method is as described above. For example, the electromagnetic radiation is emitted by an electromagnetic radiation source, e.g. an infrared LED, and distributed along electromagnetic radiation guides, e.g. optical fibers, along the surface of the RF coil device.

Advantageously, the electromagnetic radiation from the markers is captured by at least one camera, either a 2D camera or a 3D camera. The camera may be an optical or an infrared camera. In an embodiment, the camera is a digital camera, i.e. a camera in which the image 15 captured by digital image sensor, e.g. a CCD or CMO, and may be a video camera. The camera may be placed above the patient table of the MR or MR-PET imaging modality, either inside the magnet bore, or outside. For example, the camera may be attached to the ceiling or a scaffolding above the patient table, at the patient table position outside the bore, in which the patient will mount the table and the operator will place RF coil devices on the patient.

In an embodiment, the grid of visible points (wherein each visible point corresponds to a marker) which is detected by the camera is matched to a known template, which corresponds to the grid detected from the RF coil device in the first position, orientation, and/or shape which corresponds to the predefined attenuation map. This way, the predefined attenuation map of the RF coil device can be adapted to the current position of the RF coil device. The matching of points to a template results in a deformed predefined attenuation map, which is a current attenuation map. This attenuation map is then used to correct a PET image.

In an embodiment, the position and/or orientation and/or shape of the at least one coil of the RF coil device and/or of the RF coil device is determined by stereoscopy. Stereoscopy describes methods by which the position of the EM radiation markers in three-dimensional space may be determined from two 2D images acquired from (slightly) different positions or angles. Accordingly, two images acquired from different detection points of the same electromagnetic radiation emitting area are necessary. It is the same principle that is used by human beings for stereoscopic vision, i.e. combining two offset images from the left and right to give the perception of three-dimensional depth.

Using stereoscopy, the 3D position in space of the radiation markers may be determined by several 2D cameras placed around the patient table, for example at an angle of 20-70° to one another. If all markers are visible for each 2D camera, and if the pattern of the radiation markers on the RF coil device is known, 2D cameras may be sufficient to provide the 3D positions in space. In an embodiment, 2-4 2D cameras are used, i.e. the electromagnetic radiation detector comprises several 2D cameras. However, it has been discovered that the same effect may be achieved by only one 2D camera (e.g. a digital video camera, as described above). In this embodiment, the electromagnetic radiation of each or at least some of the electromagnetic radiation markers of the RF coil device is guided on at least two different optical parts to the electromagnetic radiation detector, in this case a 2D camera, using at least two mirrors, each path including at least one mirror. Thereby, it is possible to view the RF coil device from different directions and still use only one camera. If the mirrors can be moved, so that only one optical path is active at a time, the 2D camera may capture several images of the patient table from different angles one after the other. However, this requires movement of the mirrors.

In an embodiment, the electromagnetic radiation detector is a digital camera, and the electromagnetic radiation guided along different optical paths to the camera is captured by different areas of a sensor chip of the digital camera, for example a CMOS-chip. In other words, the radiation from each path is captured by a different section of the sensor chip of the (e.g. video) camera. Thereby, the image acquired by the camera is divided into several sections, each section containing an image of the markers acquired from a different angle (i.e. corresponding to a different optical path). In other words, the video chip of the camera may be divided into areas, each of the areas assigned to one path. Then the acquired signals can be assigned to specific paths depending on the section or area of the chip where it has been detected. For example, the video chip of the video camera having e.g. a resolution of 3088×2064 pixels may be divided optically into 2 or more sections/areas of equal size. Thereby, the chip is used with maximum efficiency. Moreover, the several images of the radiation markers from different orientations may be acquired simultaneously.

In order to realize different optical parts with mirrors, one may arrange two mirrors in a V-shape, i.e. at an angle of for example 60-120° to one another, wherein the mirror surfaces are at the outside of the V. The 2D camera is positioned close to the tip of the V, so that the two mirrors essentially cover the complete field of vision of the camera. The camera may view the two mirrors from below. Thereby, the optical field of vision of the camera is divided into two sections, each section belonging to one mirror. In an embodiment, the optical path is continued from each of the two mirrors of the V to one or several further mirrors, and from there to the patient table and RF coil device. In one embodiment, light from the radiation markers may take one of two optical paths to reach the camera, wherein one optical path runs to a further mirror above the patient table, from there to the left side of the V-shaped mirrors, and from there into one section of the camera. The other optical path runs to another further mirror above the patient table, from there reflected to the right side of the V-shaped mirrors, and from there into the optical camera. The further mirrors may be oriented at an angle of about 30-170° to their corresponding mirror in the V-shaped mirror. In an embodiment, four optical paths are used. In this embodiment, the two mirrors are arranged in V-shape and each divided into two sections, wherein each section captures the light from the radiation markers reflected from a different further mirror. Thus, there are four further mirrors arranged at angular distances of for example 20-60° around the patient table, wherein two mirrors project the light from the radiation markers to each mirror of the V-shape, which in turn directs the light into the 2D camera. In other words, the mirrors are arranged such that the first two mirrors divide the optical field of vision of the 2D camera in halves, and direct the optical path to the left and right, which may be in an approximate horizontal direction perpendicular to the longitudinal direction (z-direction) of the patient table, i.e. in the x-direction of the imaging modality. The other four mirrors bend the optical path back towards the patient table. Thus, the patient table is captured from above from two different angles. In an embodiment, the camera is turned around in the vertical direction (vertical meaning along the gravitational direction of Earth), so that the higher resolution of the sensor chip is perpendicular to the longitudinal z-direction of the MR main magnet.

In embodiments in which the electromagnetic radiation markers are reflectors, an optical or infrared lamp, e.g. a spotlight, may be used to illuminate the markers. The light to illuminate the markers may travel along the same optical paths as described above, and thus the lamp may be arranged next to the camera and pointing in the same direction. For example, the light of an infrared spotlight is folded or redirected by the same mirrors on its way to the RF coil device, and thus only one IR spotlight is necessary.

The electromagnetic radiation of each electromagnetic radiation marker may be guided using all paths to the electromagnetic radiation detector. For example, the video chip of the video camera having e.g. a resolution of 3088×

2064 pixels may be divided optically in 4 sections, each having a pixel size of 750×2064. This pixel size has proven a good size to capture a complete patient table having a size of around 700×2000 mm.

In an embodiment, six mirrors are used to guide the electromagnetic radiation to the one camera. Thereby, four independent paths may be generated.

In accordance with another aspect of the disclosure, a non-transitory computer-readable data storage medium encoded with programming instructions is provided. Said storage medium may be loaded into a computer system of an MR imaging modality or a hybrid MR-PET imaging modality including a magnetic resonance (MR) apparatus that comprises an MR data acquisition scanner having a radio-frequency (RF) transmitter, an RF receiver being an RF coil device, a gradient RF coil device, a memory, and optionally a positron emission tomography device, said programming instructions causing said computer system to carry out the method described above. The data storage medium may be a hard disk, SD card, SSD card, cloud server, on optical or magnetic storage medium, a CD-ROM or USB stick, etc.

In an embodiment, the data storage medium also comprises the predefined attenuation map of the RF coil device as described above.

In accordance with another embodiment of the disclosure an MR- or hybrid MR-PET imaging modality is disclosed comprising:
- a magnetic resonance apparatus having an MR data acquisition scanner comprising a gradient RF coil device,
- at least one electromagnetic radiation detector, an RF coil device as described herein,
- a storage medium in which instructions to run the MR or MR-PET imaging modality are stored, and
- a computer having access to said storage medium.

In case of a hybrid MR-PET imaging modality, a PET device may also be part of the imaging modality. Thus, to execute the method as described above, one not only has to generate the electromagnetic radiation at the markers as described above, the electromagnetic radiation should also be detected.

In one embodiment, several cameras may be positioned outside the hybrid MR-PET imaging modality to detect the emitted electromagnetic radiation. The cameras may be 2D- or 3D-cameras. In an embodiment, the cameras may be implemented as infrared sensitive high-resolution CMOS cameras. The cameras can detect the electromagnetic radiation from outside as a 3D mesh or grid of surface points. The position, orientation, and shape of the RF coil device can be detected by solving the 3D correspondence problem of these points with a known reference model of the RF coil device by simple methods known in computer vision. The predefined attenuation map of the RF coil device could be warped accordingly and copied to its position in the final attenuation map, and hence correct the loss in counts during the PET reconstruction.

Several attenuation maps of different RF coil devices may be determined at the same time. The determination of the position of the markers does not depend on the number of RF coil devices they are fixed to. It is important to know the designs of the RF coil devices to assign the markers to specific points on the surface of the RF coil devices, so that the predefined attenuation maps are adapted correctly. At least the data acquisition for several RF coil devices may be executed at the same time. In an embodiment, the EM radiation markers of different RF coil devices may use different wavelengths, so they can be distinguished from one another more easily.

In an embodiment, the storage medium is configured as described above. Then, the described method can be executed by the hybrid MR-PET imaging modality or MR imaging modality.

Two mirrors may be used which are positioned at an angle in any suitable range of angles to one another such as for example a range of 60° to 120°, 80° to 100°, etc. In an embodiment, the two mirrors are at an angle of 90°±2°, i.e. substantially perpendicular, to one another.

The described method may be executed in an MR- or hybrid MR-PET imaging modality. The guidance of the electromagnetic radiation using mirrors is disclosed with regard to the MR- or hybrid MR-PET imaging modality. Of course, this way of guiding the electromagnetic radiation can also be used executing the method of determining an attenuation map for an RF coil device.

BRIEF DESCRIPTION OF THE DRAWINGS/FIGURES

Embodiments of the disclosure are now be described with reference to the attached figures.

Parts that correspond to one another are labeled with the same reference characters in all figures FIG. 1 shows an embodiment of a hybrid MR-PET imaging modality, in accordance with one or more embodiments of the present disclosure;

DETAILED DESCRIPTION

Figure 1:
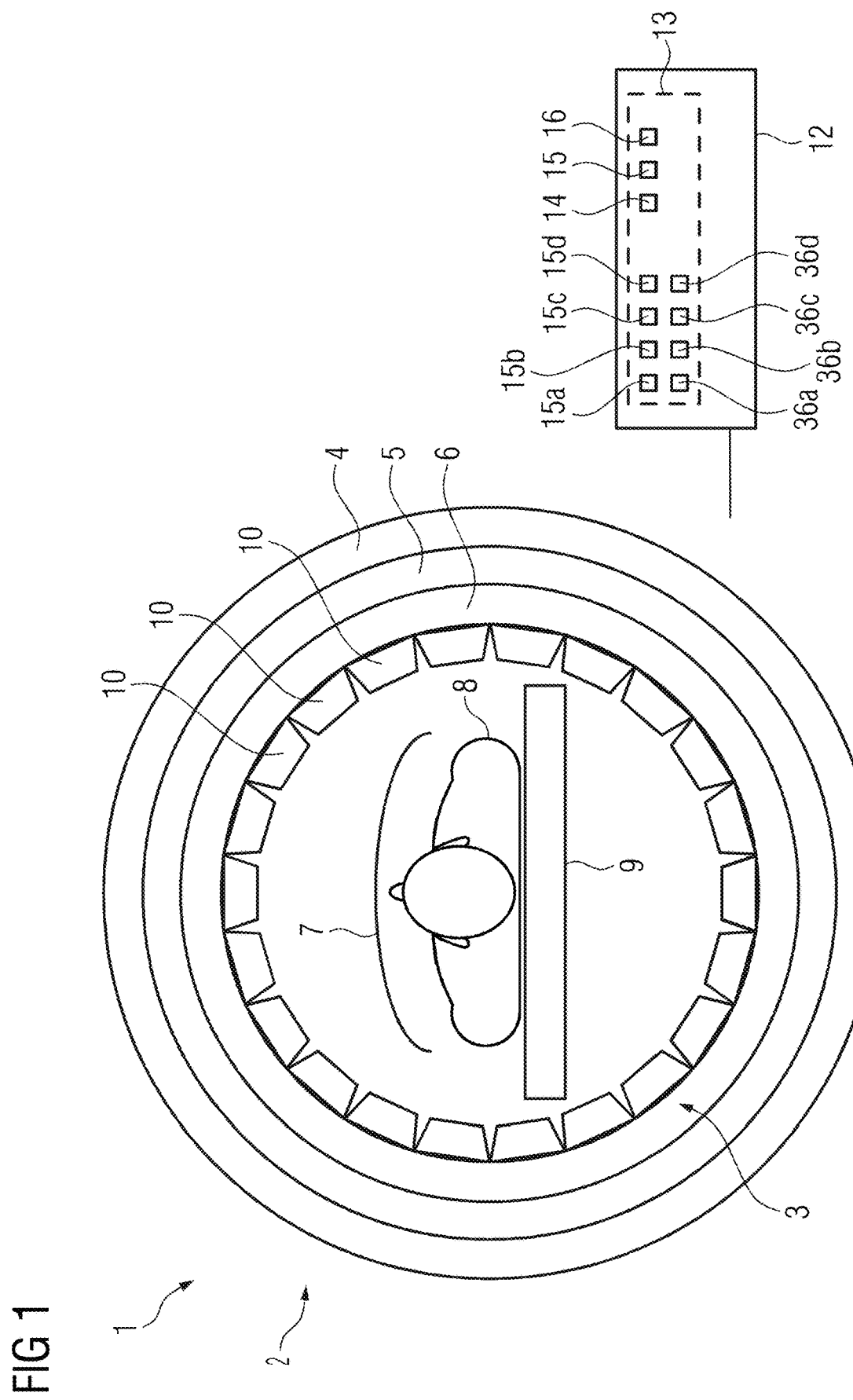

FIG. 1 shows a hybrid MR-PET imaging modality 1 having a magnetic resonance apparatus 2 and a PET device 3.

The magnetic resonance apparatus provides a magnet assembly 4 to generate the basic magnetic field BO, a transmit RF coil device 5 that may be designed as a body coil, and a gradient RF coil device 6. The RF coil device 7 or RF coil devices 7 are located on patient 8 who is positioned on a patient table 9.

The gradient RF coil device typically has three gradient coils to create gradient fields in x, y- and z-direction. The z-direction is the direction of the main magnetic field BO. PET detectors 10 of PET device 3 are positioned inside the gradient RF coil device. The less attenuating the material that is located between patient 8 and PET detectors 10, the more reliable the PET count rate is. A control computer 12 controls the operation of the hybrid MR-PET imaging modality.

The hybrid MR-PET imaging modality 1 also has a non-transitory data storage medium 13 as part of the control computer 12 or independent thereof, on which computer code for carrying out magnetic resonance measurements and PET measurements is stored. In particular, there is program code 14 to execute one or more methods in accordance with the embodiments described herein to determine an attenuation map for an RF coil device.

On data storage medium 13, there is also stored a predefined attenuation map 15 of RF coil device 7. If there were more than one RF coil device 7 in use, of course a predefined attenuation map for each RF coil device 7 can be held available. The RF coil device 7 is used to read out the MR measurement signal, which can be an echo signal. Further components of the hybrid MR-PET imaging modality 1 are not shown for clarity.

Figure 2:
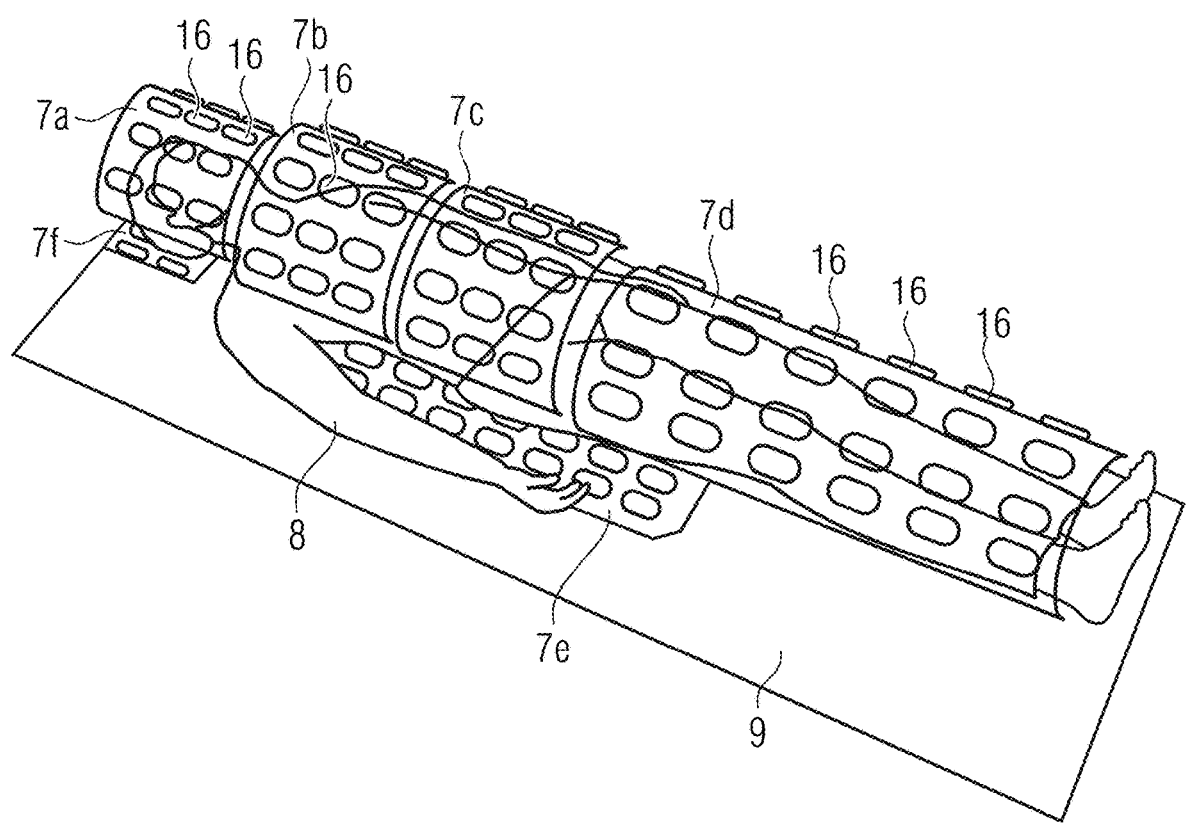
FIG. 2 shows several RF coil devices in detail, in accordance with one or more embodiments of the present disclosure.

FIG. 2 shows six RF coil devices 7a, 7b, 7c, 7d, 7e and 7f in detail. The six RF coil devices are positioned on a patient 8 at the same time. Embodiments of the RF coil devices 7a to 7f are described in more detail in FIGS. 3 to 8. FIG. 2 shows a possible position of RF coil devices 7a to 7f on a patient 8. Additionally, one can see the possible change of the positions, orientations, and shapes of coils 16 of an RF coil device 7a to 7f depending on the shape of patient 8.

In FIGS. 3 to 8 only some coils, electromagnetic radiation markers etc. have reference signs for clarity.

Figure 3:
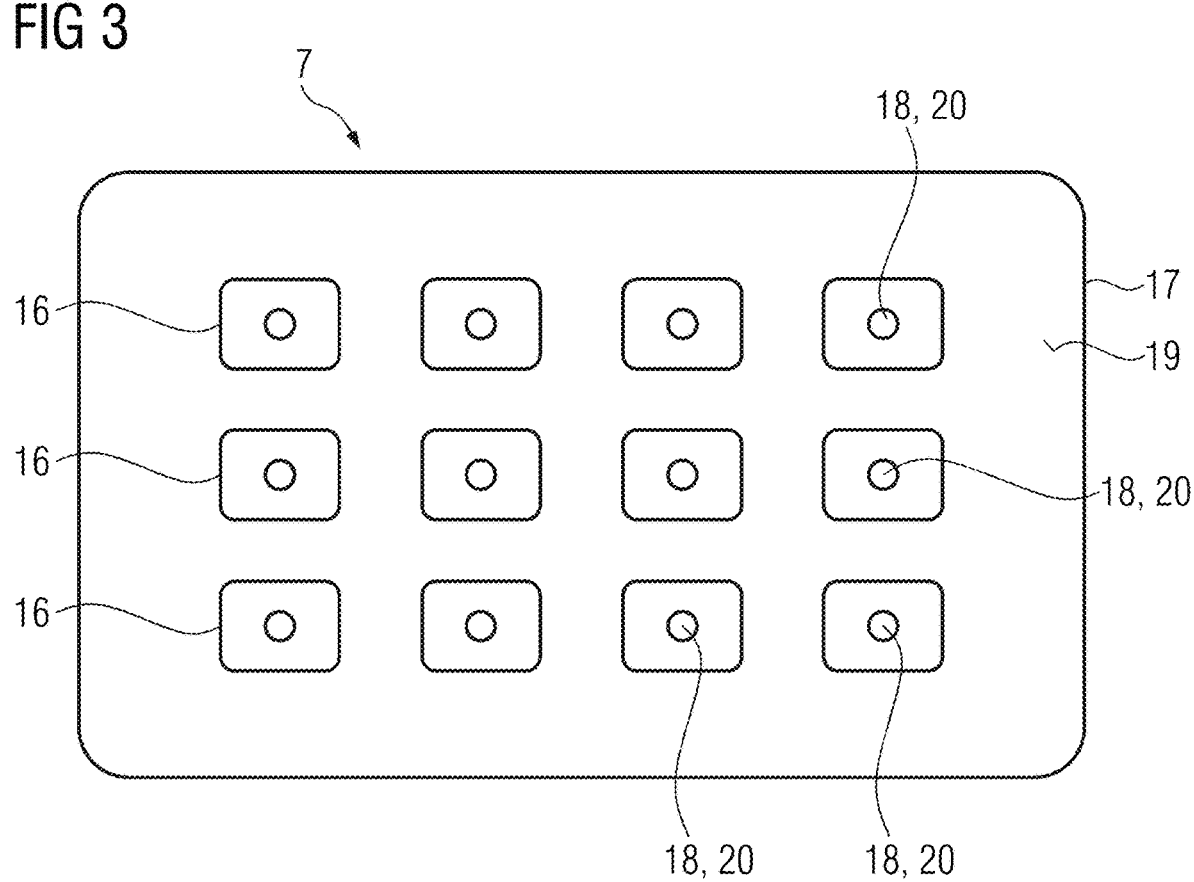
FIG. 3 shows an RF coil device in a first embodiment in top view, in accordance with one or more embodiments of the present disclosure.

FIG. 3 shows an RF coil device 7 in a first embodiment. RF coil device 7 may be identified with one of RF coil devices 7a to 7f of FIG. 2. Each of the RF coil devices 7a to 7f may be formed as RF coil device 7 of FIG. 3.

RF coil device 7 has a plurality of coils 16. Coils 16 are designed as surface coils and are flexible in shape. Housing 17 of the RF coil device 7 is also flexible in shape. Therefore, also the position and orientation of coils 16 can vary.

To determine the position, orientation, and shape of coils 16 there are electromagnetic radiation markers 18 provided on surface 19 of RF coil device 7. In the embodiment shown in FIG. 3 the electromagnetic radiation markers 18 are designed as LEDs (light emitting diodes), e.g. as infrared LEDs 20. Commercially available infrared LEDs typically emit light having one of the following wavelengths: 840 nm, 850 nm, 875 nm, 880 nm, 885 nm, 890 nm, 940 nm and 950 nm. Therefore, these work in the near-infrared radiation range. There is at least one infrared LED 20 per coil 16.

If the position of the infrared LEDs 20 is determined in 3D space, also the position, orientation, and shape of coils 16 and housing 17 can be identified.

Figure 4:
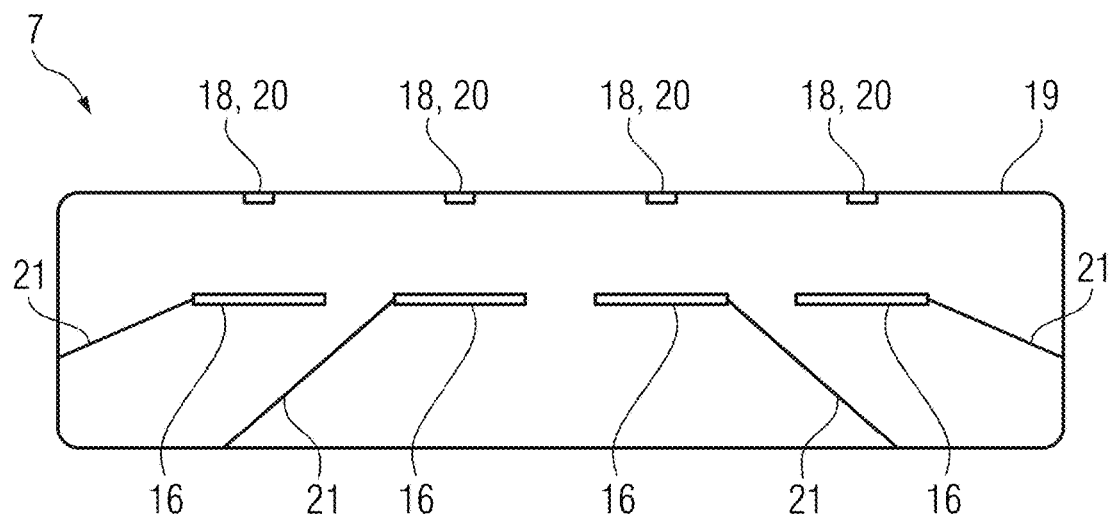
FIG. 4 shows a cross sectional view of the RF coil device according to FIG. 3, in accordance with one or more embodiments of the present disclosure.

FIG. 4 shows a cross-sectional view of RF coil device 7 of FIG. 3. It can be seen that infrared LEDs 20 are arranged at the surface 19 of RF coil device 7. Additionally, an exemplary position of the conductors 21 of coils 16 is shown. An advantage of this embodiment is the possibility of controlling the electromagnetic radiation markers 18 separately. A disadvantage can be found in the necessity of a power supply for each infrared LED 20.

Figure 5:
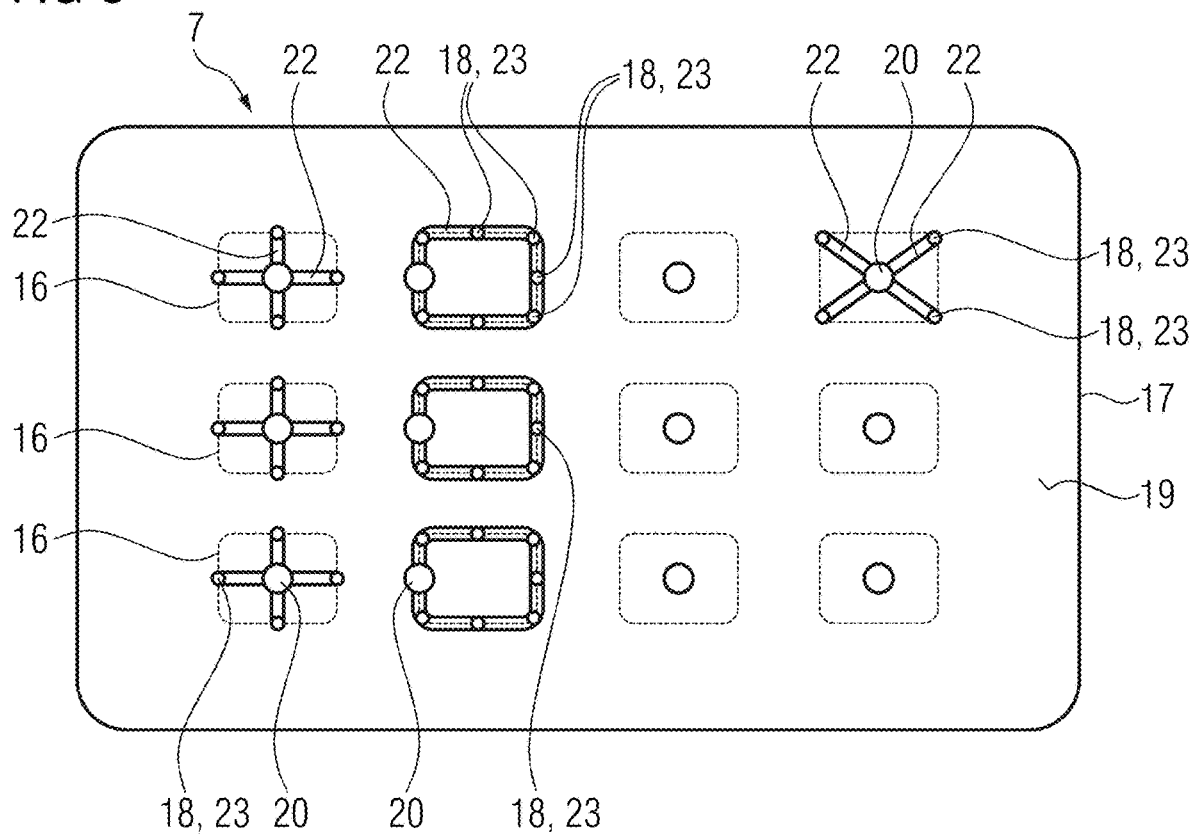
FIG. 5 shows an RF coil device in a second embodiment in top view, in accordance with one or more embodiments of the present disclosure.

FIG. 5 shows a second embodiment of an RF coil device 7. Again, each of the RF coil devices 7a to 7f may be formed as the RF coil device 7 shown in FIG. 5. In FIG. 5, the coils 16 are indicated in dashed lines, as the coils are inside the coil housing and are not visible when looking at the RF coil device. In this embodiment, the light of infrared LEDs 20 is guided by light guides 22 to surface 19, and the electromagnetic radiation markers 18 are formed by the endings or openings 23 of light guides 22. There may be several openings 23 at one light guide 22. There are several possibilities to position light guides 22 and openings 23 to mark the position of the coils 16. These are shown from left to right. In the left "column" comprising three coils 16, each coil has one LED 20 in the center, and four short optical fibers 22 extend to four sides, in this case top, bottom, left, and right, where the optical fibers 22 end at a position just above the perimeter of coils 16 and therefore may indicate the coil circumference. The end of each optical fiber 22 emits light and therefore corresponds to an optical marker 18. In the column of three coils one further to the right, each coil also has one LED 20 and supplies one optical fiber 22, which runs along the circumference of the coil 16 and has openings 23 in the coating at non-regular intervals so that the rectangle of the coil 16 is defined by openings in the corners and in the center of each side. In the column of three coils one further to the right, one LED 20 is situated in the center of each coil 16, and no optical fibers are present. It would also be possible to use only one LED, and to have one optical fiber connecting the centers of the several coils, and having one opening 23 at the center of each coil. In the right most column, also each coil has one LED 20 in the center, and four optical fibers extend into the corners of the rectangle of the coil, thereby forming an X, wherein the end 23 of the optical fiber is situated at the corner of the rectangular shape of the coil. In an embodiment, the coils 16 are arranged inside the housing, and the LEDs and optical fibers are arranged at or near the outer surface of the housing, for example within respective channels, notches, and/or recesses within the housing. As an example, the openings 23 in the optical fibers and/or their ends are open towards the outside to allow the emission of electromagnetic radiation in the specified frequency ranges. In an embodiment, the LEDs and optical fibers are embedded into the housing, whereas the ends of the optical fibers, which emit radiation, are exposed towards the outside, as are any locations where the optical fiber may include openings acting as markers. In some embodiments, several coils 16 may share one LED, and optical fibers may run along several coils 16 and have an opening 23 to indicate each coil.

Figure 6:
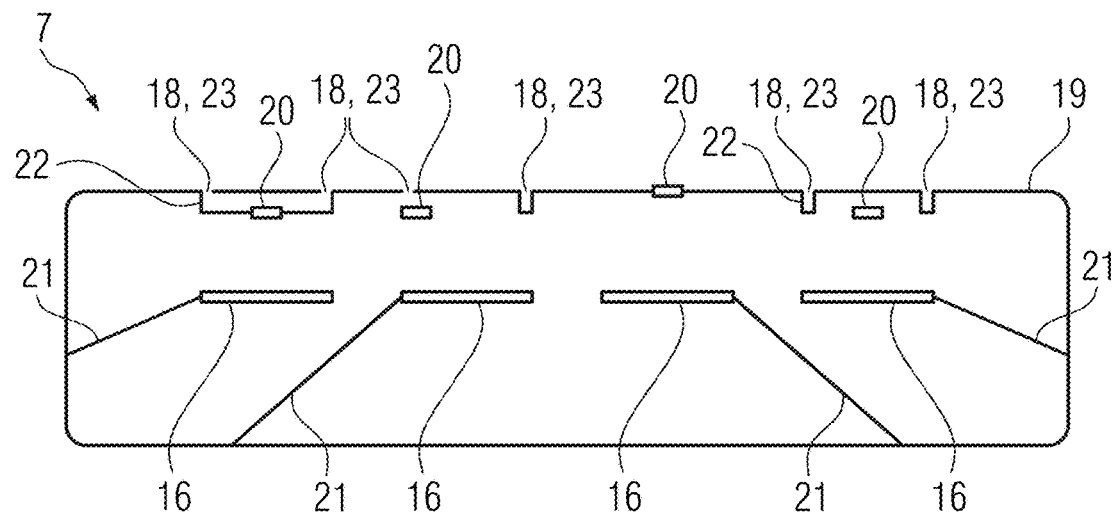
FIG. 6 shows a cross sectional view of the RF coil device according to FIG. 5.

FIG. 6 shows a cross-sectional view of RF coil device 7 of FIG. 5. FIG. 6 also shows the coils 16 together with the conductor 21 connecting each coil. An electrical conductor is also present to provide electrical current to each LED 20, but is not shown. In the leftmost example shown in FIG. 6 (which corresponds to the leftmost column of coils 16 shown in FIG. 5), LEDs 20 are embedded into the housing 17 and are not visible from the outside. The light of LEDs 20 is guided to surface 19 by light guides 22. The light leaves light guides 22 through openings 23, which are at the upper side of the RF coil device. In the example one further to the right, the LED 20 is embedded into the housing, and the optical fiber is led in a notch following the circumference of the coil 16 below, which is open towards the outer surface so that openings 23 are visible. In the third example from the left, where the coils 16 only have one LED in the center, the LED 20 is not embedded, but is situated on the surface of housing 17 so that its light is visible from the outside. In the right most example, an embedded LED 20 again supplies four optical fibers 22, which lead towards the outer surface of the housing.

An advantage of this embodiment is the low number of infrared LEDs 20 compared to electromagnetic radiation markers 18. A disadvantage can be found in the missing availability of a separate control of the electromagnetic radiation markers 18.

Figure 7:
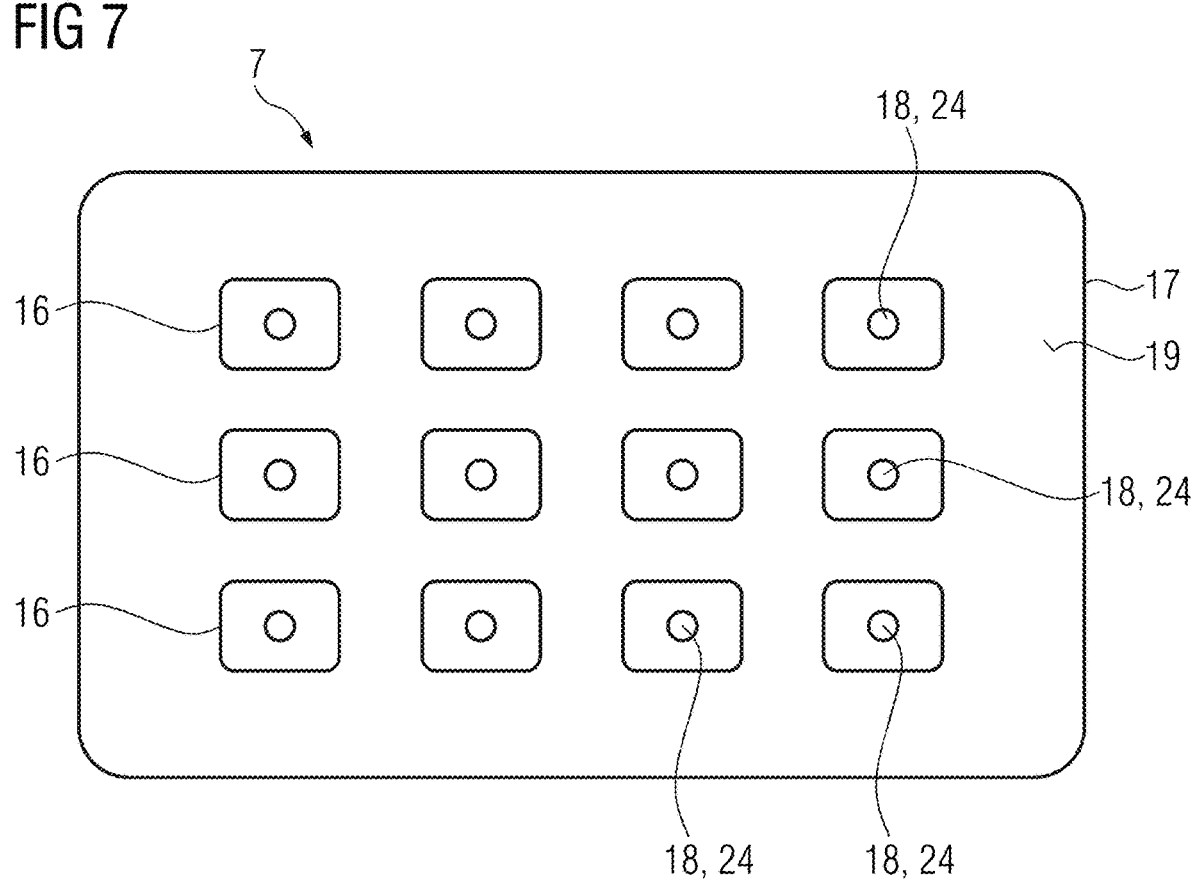
FIG. 7 shows an RF coil device in a third embodiment in top view, in accordance with one or more embodiments of the present disclosure.

FIG. 7 shows a third embodiment of an RF coil device 7. Again, each of the RF coil devices 7*a* to 7*f* may be formed as RF coil device 7 of FIG. 7. In this embodiment, there are no infrared LEDs 20 positioned inside housing 17. There are only reflectors 24 located at the surface 19 of RF coil device 7.

Figure 8:
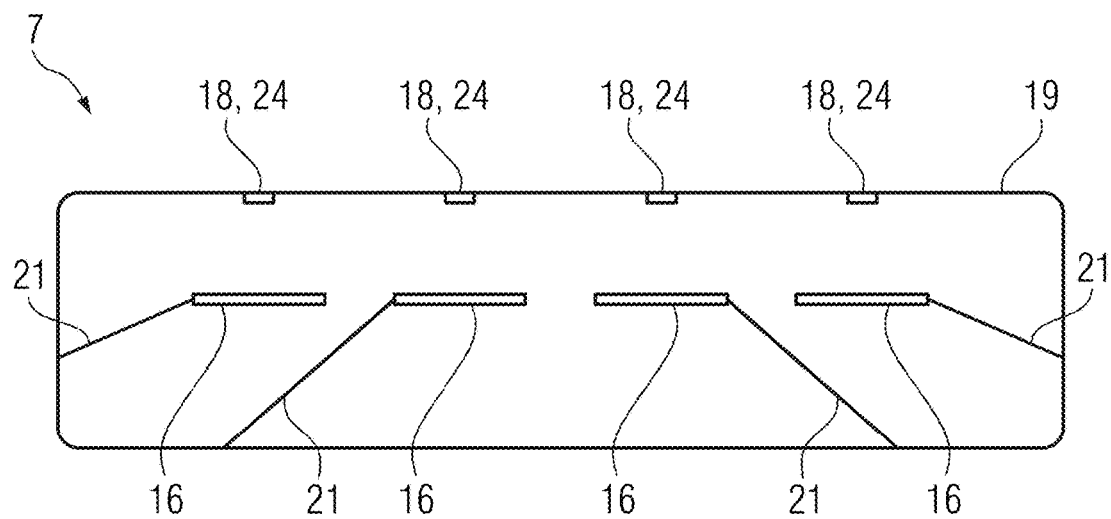
FIG. 8 shows a cross sectional view of the RF coil device according to FIG. 7, in accordance with one or more embodiments of the present disclosure.

FIG. 8 shows a cross sectional view of RF coil device 7 of FIG. 7. There one can see that each reflector 24 is positioned above one coil 16, e.g. at the center of coil 16.

An advantage of this embodiment is the realization without changes inside housing 17. A disadvantage can may be the difficulty to illuminate reflectors 24 equally.

Of course, the embodiments of FIGS. 3, 5, and 7 can be combined with one another in whole or in part. Then, one or several infrared LEDs 20 may be positioned at surface 19 and one or several LEDs 20 may be positioned within housing 19. The light of the latter ones is guided by light guides 22 to surface 19. Additionally, there may be reflectors 24 at surface 19.

Each of the embodiments according to FIGS. 3, 5, and 7 may be realized alone, in combination with a second embodiment, or all three embodiments altogether.

If there is more than one RF coil device 7, e.g. as disclosed in FIG. 2, then the electromagnetic radiation markers may be realized differently for each RF coil device. Of course, it is preferred to produce the RF coil devices 7 consistently to reduce production costs. But if there is a need to mix the embodiments it is possible to do so.

FIGS. 3 to 8 have shown several embodiments how to position and realize markers 18 to generate an electromagnetic radiation marker signal. In the following figures, several ways will be described how to receive the signals.

Figure 9:
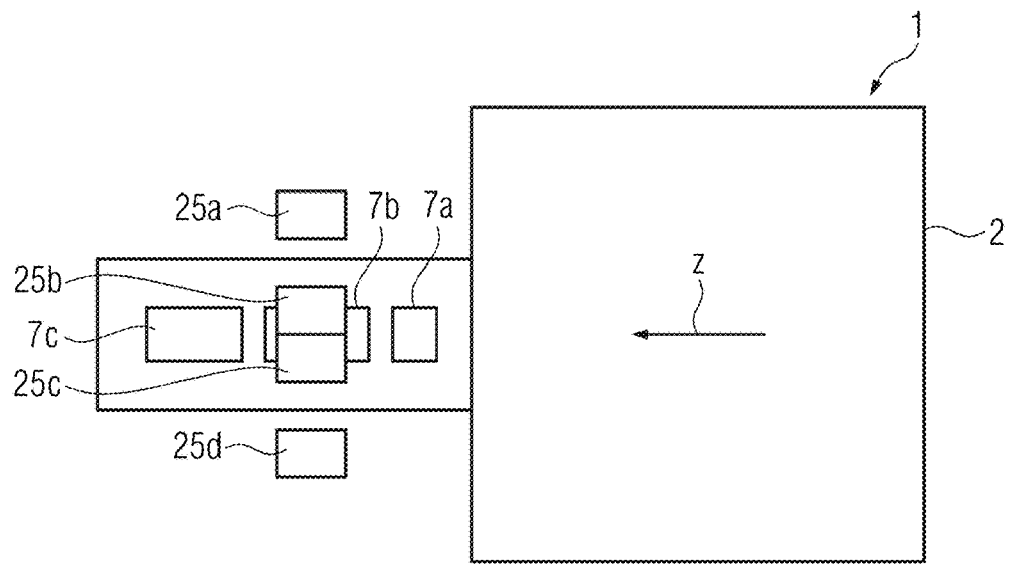
FIG. 9 shows a detector arrangement, in accordance with one or more first embodiments of the present disclosure.

FIG. 9 shows a view from above on an embodiment where several infrared sensitive high-resolution cameras 25*a*, 25*b*, 25*c* and 25*d* are positioned circularly around the z axis of hybrid MR-PET imaging modality 1. Cameras 25*a*, 25*b*, 25*c*, and 25*d* are oriented towards the patient table 9 and can be used to perform a stereoscopic determination of the position of electromagnetic radiation markers 18 of RF coil devices 7 in 3D space. These positions are used to calculate the position, orientation and shape of coils 16. Thereby a predefined attenuation map 15 may be warped into an attenuation map, which then is a current attenuation map. This method can be performed for each RF coil device 7 in use.

Figure 10:
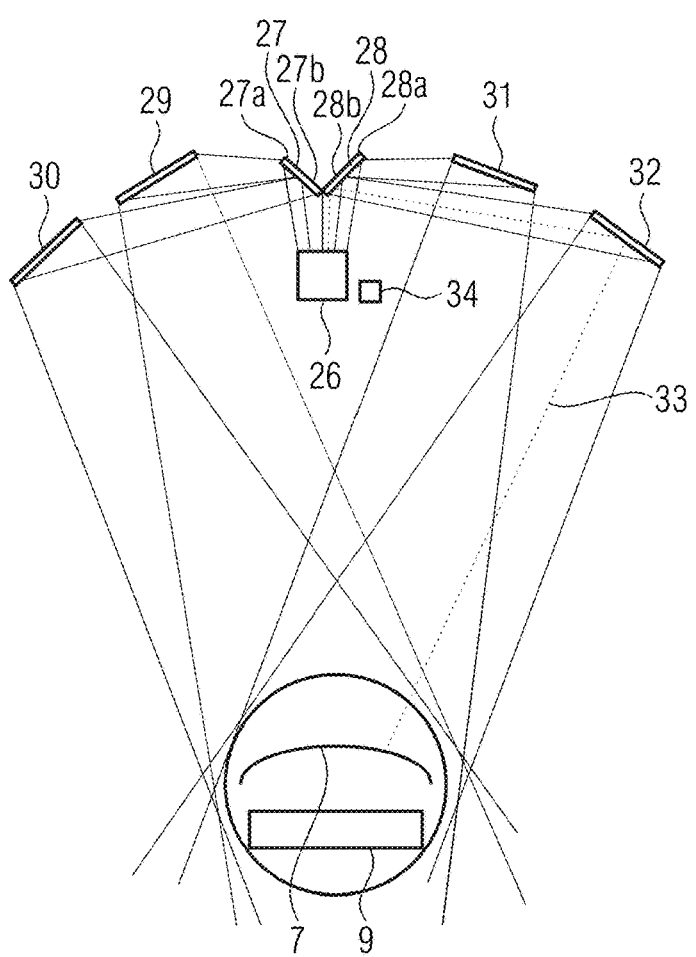
FIG. 10 shows a cross-sectional view of a detector arrangement in accordance with one or more second embodiments of the present disclosure.

FIG. 10 shows a cross-section of a second embodiment differing to FIG. 9 in the usage of mirrors. This allows a reduction of the number of cameras to one camera 26. As an example, camera 26 is an infrared sensitive high-resolution CMOS camera 26.

Two mirrors 27 and 28 are located in front of camera 26. Mirror 27 and 28 are positioned at any suitable range with respect to one another, such as for instance in a range of 60° to 120°, 80° to 100°, etc. In an embodiment, the mirrors may be at an angle of 90°±2°, so as to be substantially perpendicular to one another. Mirrors 27 and 28 are arranged in a V-shape, wherein the camera 26 views the V from below, so that its field of vision is divided in halves, each half capturing reflections from one of mirrors 27 and 28.

On the left side of mirror 27 there are two mirrors 29 and 30, and on the right side of mirror 28 there are two mirrors 31 and 32. Each mirror 29 to 32 is directed towards the patient table 9 with the RF coil device 7 at a different angle. Mirrors 29 to 32 are positioned circularly around the z axis of hybrid MR-PET imaging modality 1. Thus, the mirrors reflect light beams 33 to different areas 27*a*, 27*b*, 28*a*, and 28*b* of mirrors 27 and 28. In other words, the areas of each mirror 27, 28 is also divided into two halves, wherein each half is receiving light from a different mirror, for example the upper half 27*a* of mirror 27 receives light from mirror 29, and the lower half 27*b* from mirror 30. On the right side, the upper half 28*a* of mirror 28 is illuminated by mirror 31, and the lower half 28*b* is illuminated by mirror 32. Hence, the same point on RF coil device 7 is monitored by four different mirrors, and therefore from four different angles.

The light of each electromagnetic radiation marker 18 thus is guided on four paths to camera 26. This allows to determine its position in 3D space.

Optionally, there may be an IR emitter 34 if at least some of the electromagnetic radiation markers are designed as reflectors 24. As an example, one single IR emitter may be used. This is an additional advantage of the usage of the mirrors.

Figure 11:
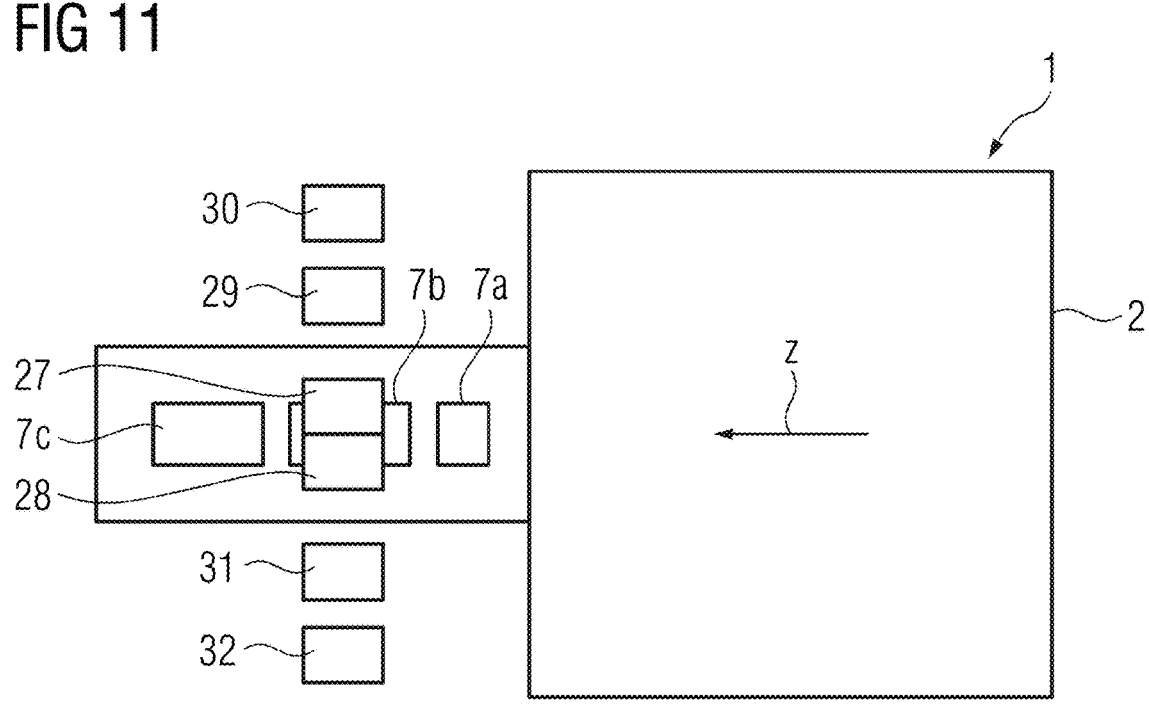
FIG. 11 shows the hybrid MR-PET imaging modality of FIG. 10 in top view, in accordance with one or more embodiments of the present disclosure.

FIG. 11 shows a top view on the arrangement according to FIG. 10. There one can see the axial position of mirrors 27 to 32. The mirrors 27 to 32 are located in front of and above hybrid MR-PET imaging modality 1. There, enough room is available to position mirrors 27 to 32 as well as camera 26. When the patient table 9 is outside and in front of the hybrid MR PET imaging modality 1, i.e. in a position where the patient 8 will mount the patient table, also the RF coil device 7 will be already positioned on patient 8 and therefore in that position it will have during the MR-PET examination.

Figure 12:
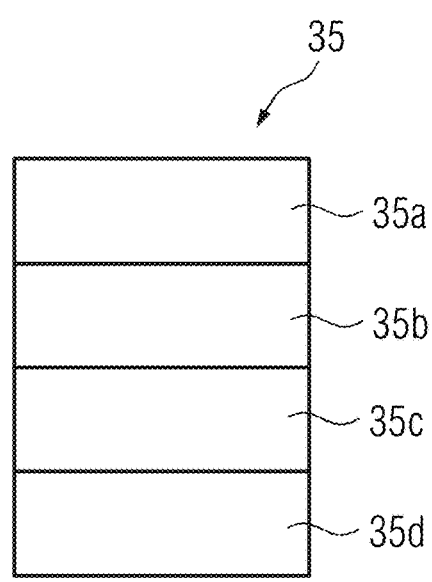
FIG. 12 illustrates a video chip in top view, in accordance with one or more embodiments of the present disclosure.

FIG. 12 shows a video chip 35 of camera 26 in top view. Area 35*a* is assigned to area 27*a*, area 35*b* to area 27*b*, area 35*c* to area 28*b*, and area 35*d* to area 28*a*. Video chip 35 may have 3088×2064 detection elements (pixels). Each area 35*a* to 35*d* then has about 750×2064 detection elements. This resolution of each area fits to the area of patient table 9, which has about 700 mm×2000 mm. The advantage of the embodiment according to FIGS. 10 to 12 is the possibility of performing stereography with only one camera 26. The acquisitions are automatically synchronous.

Please note that the embodiments according to FIGS. 3 to 8 are independent of the embodiments according to FIGS. 9 to 12. In other words, the creation of the light signals is independent of the receiving arrangement, although these embodiments may be used in combination with one another.

Figure 13:
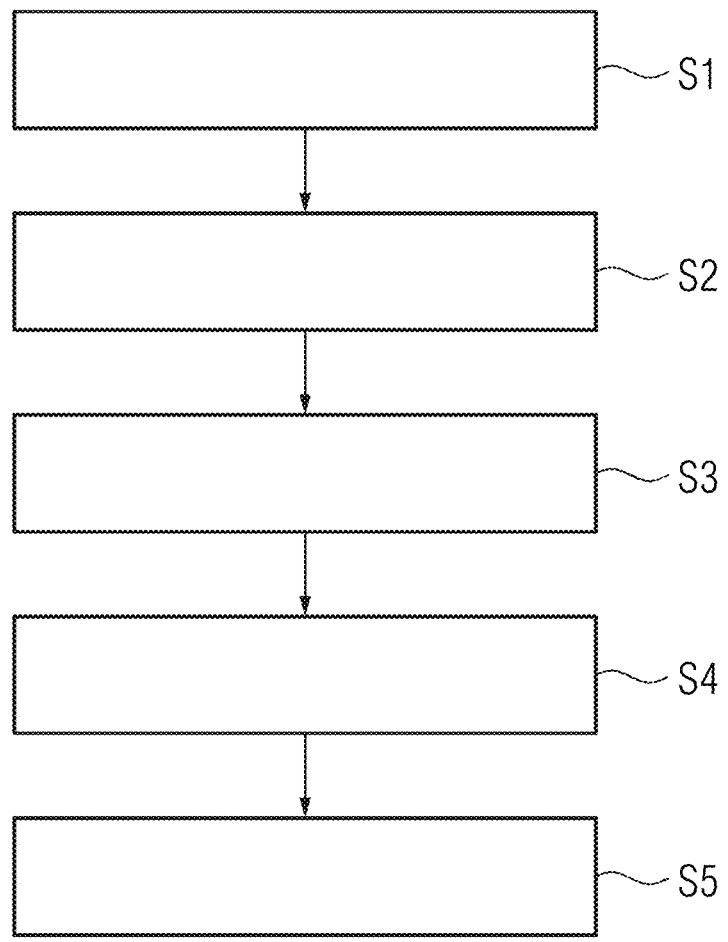
FIG. 13 illustrates a flow diagram, in accordance with one or more embodiments of the present disclosure.

FIG. 13 shows a method to determine an attenuation map for an RF coil device.

In step S1, patient 8 is positioned on a patient table 9. After that, one or more RF coil devices 7*a*, 7*b*, 7*c*, and 7*d* are laid on patient 8. Patient table 9 is driven to the position of FIG. 10 if necessary.

Then, in step S2 the infrared LEDs 20 and/or IR emitter 34 are switched on. Camera 26 or cameras 25*a*, 25*b*, 25*c*, and 25*d* acquire images of RF coil devices 7*a*, 7*b*, 7*c*, and 7*d*. Please note that RF coil devices 7*e* and 7*f* usually do not change their position and therefore are not mentioned here. If it was necessary of course also markers 18 are mounted on RF coil devices 7e and 7f.

In step S3, the images acquired with camera 26 or cameras 25a to 25d are used determine the position of the electromagnetic radiation markers 18 in 3D space.

These positions are then taken in step S4 to calculate the position, orientation, and shape of coils 16 of RF coil devices 7a, 7b, 7c and 7d.

In step S5, the information obtained in step S4 is used to warp predefined attenuation maps 15a to 15d, one for each of RF coil devices 7a, 7b, 7c, and 7d, to attenuation maps 36a, 36b, 36c, and 36d.

Depending on the MR-PET experiment, it may be sufficient to determine an attenuation map for one of coils 7a to 7d. The attenuation maps are used to correct the signals detected with the PET detectors 10. They cover only a short range in axial direction, hence only for this range attenuation maps are needed.

Embodiments also include having several LEDs per coil 16 that can be controlled independently to be able to switch individual surface points on and off to simplify the correspondence problem.

In step S6, attenuation maps 36a to 36d are used during the reconstruction of PET images out of the acquired PET signals.

Thus, the determination of attenuation maps 36a to 36d can be executed before, during, or after the MR-PET experiments. It has only to be done before the reconstruction of the MR-PET images.

What is claimed is:

1. A radio frequency (RF) coil device for a magnetic resonance (MR) imaging modality or a hybrid MR-positron emission tomography (PET) imaging modality, comprising:
   a plurality of RF coils;
   a housing for the plurality of RF coils; and
   a marker arrangement comprising a plurality of marker characteristic patterns, each one of the plurality of marker characteristic patterns comprising:
      a plurality of electromagnetic radiation markers disposed at an outer surface of the housing, and being identified with a location of a respective one of the plurality of RF coils,
      at least one electromagnetic radiation source configured to emit electromagnetic radiation, and
      at least one electromagnetic radiation guide comprising an optical fiber, light guide, or hollow conductor, which is coupled to the at least one electromagnetic radiation source and configured to route the electromagnetic radiation emitted from the at least one electromagnetic radiation source to each respectively coupled one of the plurality of electromagnetic radiation markers,
   wherein each one of the plurality of electromagnetic radiation markers is formed by way of an emission, in each one of a plurality of openings in a respectively coupled electromagnetic radiation guide, of electromagnetic radiation provided by the at least one electromagnetic radiation source, and
   wherein the electromagnetic radiation is within at least one of the ultraviolet, visible, infrared (IR), or Terahertz spectrum.

2. The RF coil device of claim 1, wherein the marker arrangement further comprises, for one of the plurality of marker characteristic patterns, at least one light-emitting diode (LED) configured as the at least one electromagnetic radiation source and the at least one electromagnetic radiation guide is configured to distribute the electromagnetic radiation from the LED over the outer surface of the housing.

3. The RF coil device of claim 2, wherein the at least one electromagnetic radiation guide has a coating and is configured to emit electromagnetic radiation from one or more openings in the coating.

4. The RF coil device of claim 1, wherein each one of the plurality of electromagnetic radiation markers is configured to emit infrared electromagnetic radiation at a wavelength between 700 nm and 30 µm.

5. The RF coil device of claim 1, wherein for one of the plurality of marker characteristic patterns, the at least one electromagnetic radiation guide is configured to route the electromagnetic radiation emitted from a respectively coupled electromagnetic radiation source to the respective plurality of electromagnetic radiation markers via containment within the at least one electromagnetic radiation guide.

6. The RF coil device of claim 1, wherein, for each one of the plurality of marker characteristic patterns, the electromagnetic radiation source is from among a plurality of electromagnetic radiation sources, and
   wherein a number of the plurality of electromagnetic radiation sources is less than a number of the respective plurality of electromagnetic radiation markers.

7. The RF coil device of claim 1, wherein the marker characteristic pattern formed by each one of the plurality of electromagnetic radiation markers is different from one another.

8. The RF coil device of claim 1, wherein, for each one of the plurality of marker characteristic patterns, the at least one electromagnetic radiation source comprises a single electromagnetic radiation source that is integrated within the RF coil device and disposed at a center of each respective one of the plurality of RF coils.

9. The RF coil device of claim 1, wherein the plurality of RF coils are configured to receive and/or transmit magnetic resonance (MR) signals, and
   wherein the electromagnetic radiation is different than the MR signals.

10. A method to determine one or more properties of at least one radio frequency (RF) coil of an RF coil device, the method comprising:
   positioning an RF coil device on a patient table of a magnetic resonance (MR) imaging modality or a hybrid MR-positron emission tomography (PET) imaging modality, the RF coil device including a plurality of RF coils;
   detecting electromagnetic radiation emitted from a plurality of electromagnetic radiation markers on a surface of the RF coil device via an electromagnetic radiation detector,
   wherein the plurality of electromagnetic radiation markers are part of a marker arrangement comprising a plurality of marker characteristic patterns, each one of the plurality of marker characteristic patterns comprising a plurality of electromagnetic radiation markers identified with a location of a respective one of the plurality of RF coils, and comprising at least one electromagnetic radiation guide comprising an optical fiber, light guide, or hollow conductor, which is coupled to at least one electromagnetic radiation source and configured to route the electromagnetic radiation emitted from the at least one electromagnetic radiation source to each respectively coupled one of the plurality of electromagnetic radiation markers, wherein each one of the plurality of electromagnetic radiation markers is formed by way of an emission, in each one of a plurality of openings in a respectively coupled electromagnetic radiation guide, of electromagnetic radiation provided by the at least one electromagnetic radiation source, wherein the electromagnetic radiation is within at least one of the ultraviolet, visible, infrared (IR), or Terahertz spectrum; and determining at least one of a position, orientation, or shape of the plurality of RF coils using the detected electromagnetic radiation.

11. The method of claim 10, further comprising:

providing a predefined attenuation map of the RF coil device;

determining a corrected attenuation map for the RF coil device by transforming the predefined attenuation map using at least one of the determined position, orientation, or shape of the plurality of RF coils; and correcting a PET image acquired from the patient in the hybrid MR-PET imaging modality using the corrected attenuation map.

12. The method of claim 10, further comprising:

guiding, via at least two different optical paths, electromagnetic radiation of each one of the plurality of electromagnetic radiation markers to an electromagnetic radiation detector using at least two mirrors, wherein each of the at least two different optical paths includes at least one mirror.

13. The method of claim 12, wherein the electromagnetic radiation detector is a digital camera, and wherein the electromagnetic radiation that is guided along the at least two different optical paths to the digital camera is captured by different areas of a sensor chip of the digital camera.

14. The method of claim 10, wherein the act of determining at least one of the position, orientation, or shape of the plurality of RF coils comprises determining the at least one of the position, orientation, or shape of the plurality of RF coils using stereoscopy.

15. A non-transitory computer-readable data storage medium encoded with programming instructions that, when executed by control computer of a magnetic resonance (MR) based imaging modality, cause the MR-based imaging modality to:

detect electromagnetic radiation emitted from a plurality of electromagnetic radiation markers on a surface of a radio frequency (RF) coil device via an electromagnetic radiation detector, the RF coil device including a plurality of RF coils, wherein the plurality of electromagnetic radiation markers are part of a marker arrangement comprising a plurality of marker characteristic patterns, each one of the plurality of marker characteristic patterns comprising a plurality of electromagnetic radiation markers identified with a location of a respective one of the plurality of RF coils, and comprising at least one electromagnetic radiation guide comprising an optical fiber, light guide, or hollow conductor, which is coupled to at least one electromagnetic radiation source and configured to route the electromagnetic radiation emitted from the at least one electromagnetic radiation source to each respectively coupled one of the plurality of electromagnetic radiation markers, wherein each one of the plurality of electromagnetic radiation markers is formed by way of an emission, in each one of a plurality of openings in a respectively coupled electromagnetic radiation guide, of electromagnetic radiation provided by the at least one electromagnetic radiation source, and wherein the electromagnetic radiation is within at least one of the ultraviolet, visible, infrared (IR), or Terahertz spectrum, wherein the RF coil device is positioned on a patient table of the MR-based imaging modality that includes an MR imaging modality or a hybrid MR-positron emission tomography (PET) imaging modality; and determine at least one of a position, orientation, or shape of the plurality of RF coils using the detected electromagnetic radiation.

16. A magnetic resonance (MR) based imaging modality, comprising:

a magnetic resonance apparatus having an MR data acquisition scanner including a gradient coil arrangement;

at least one electromagnetic radiation detector;

a housing including a plurality of RF coils; and a marker arrangement comprising a plurality of marker characteristic patterns, each one of the plurality of marker characteristic patterns comprising:

a plurality of electromagnetic radiation markers disposed at an outer surface of the housing, each one of the plurality of electromagnetic radiation markers being identified with a location of a respective one of the plurality of RF coils, and comprising at least one electromagnetic radiation guide comprising an optical fiber, light guide, or hollow conductor, which is coupled to at least one electromagnetic radiation source and is configured to route the electromagnetic radiation emitted from the at least one electromagnetic radiation source to each respectively coupled one of the electromagnetic radiation markers, wherein each of the plurality of electromagnetic radiation markers is formed by way of an emission, in each one of a plurality of openings in a respectively coupled electromagnetic radiation guide, of electromagnetic radiation provided by the at least one electromagnetic radiation source, and wherein the electromagnetic radiation is within at least one of the ultraviolet, visible, infrared (IR), or Terahertz spectrum.

17. The MR based imaging modality of claim 16, further comprising:

at least one mirror configured to reflect electromagnetic radiation emitted from each one of the plurality of electromagnetic radiation markers to the at least one electromagnetic radiation detector.

* * * * *